United States Patent
Ouchi (10) Patent No.: US 7,564,034 B2
(45) Date of Patent: Jul. 21, 2009

(54) TERAHERTZ SENSING APPARATUS USING A TRANSMISSION LINE

(75) Inventor: Toshihiko Ouchi, Kanagawa-ken (JP)

(73) Assignee: Canon Kabushiki Kaisha, Tokyo (JP)

( * ) Notice: Subject to any disclaimer, the term of this patent is extended or adjusted under 35 U.S.C. 154(b) by 487 days.

(21) Appl. No.: 10/566,238

(22) PCT Filed: Jul. 27, 2005

(86) PCT No.: PCT/JP2005/014146

§ 371 (c)(1),
(2), (4) Date: Jan. 30, 2006

(87) PCT Pub. No.: WO2006/011636

PCT Pub. Date: Feb. 2, 2006

(65) Prior Publication Data

US 2006/0197021 A1    Sep. 7, 2006

(30) Foreign Application Priority Data

Jul. 30, 2004 (JP) ............... 2004-223665
May 27, 2005 (JP) ............... 2005-154772

(51) Int. Cl.
*G01J 5/02* (2006.01)
(52) U.S. Cl. .................................. 250/340
(58) Field of Classification Search ........... 250/343, 250/340
See application file for complete search history.

(56) References Cited

U.S. PATENT DOCUMENTS

| | | | |
|---|---|---|---|
| 5,586,131 A | 12/1996 | Ono et al. | 372/19 |
| 5,659,560 A | 8/1997 | Ouchi et al. | 372/27 |
| 5,699,373 A | 12/1997 | Uchida et al. | 372/27 |
| 5,710,430 A * | 1/1998 | Nuss | 250/358.1 |
| 5,729,017 A * | 3/1998 | Brener et al. | 250/338.1 |
| 5,764,670 A | 6/1998 | Ouchi | 372/45 |

(Continued)

FOREIGN PATENT DOCUMENTS

EP    0 519 250    12/1992

(Continued)

OTHER PUBLICATIONS

O. Mitrofanov, et al., Terahertz near-field microscopy based on a collection mode detector, Appl. Phys. Lett. vol. 77, 2000, p. 3496-3498.

(Continued)

*Primary Examiner*—David P Porta
*Assistant Examiner*—Jessica L Eley
(74) *Attorney, Agent, or Firm*—Fitzpatrick, Cella, Harper & Scinto (57) ABSTRACT

A sensing apparatus is provided which comprises a chip (20) in which a transmission line (2) for propagating an electromagnetic wave is formed on a substrate (1), an electromagnetic wave generator (7) for generating an electromagnetic wave (10), a coupling means (9), and a detector (5) for detecting a propagation state of an electromagnetic wave at an arbitrary location on the transmission line, of the electromagnetic wave propagating through the transmission line (2). An interaction between an object (4) disposed in the vicinity of the transmission line (2) and the electromagnetic wave is detected by the detector (5) to sense a spatial interaction state of the object (4) with the electromagnetic wave.

13 Claims, 6 Drawing Sheets

U.S. PATENT DOCUMENTS

| | | | | |
|---|---|---|---|---|
| 5,789,750 | A | | 8/1998 | Nuss .................. 250/338.1 |
| 5,936,237 | A | * | 8/1999 | van der Weide ............ 250/234 |
| 5,952,818 | A | * | 9/1999 | Zhang et al. .................. 324/96 |
| 6,320,191 | B1 | * | 11/2001 | Rudd ...................... 250/341.1 |
| 6,828,558 | B1 | | 12/2004 | Arnone .................. 250/341.1 |
| 6,854,901 | B1 | | 2/2005 | Ouchi ........................ 385/89 |
| 7,062,116 | B2 | | 6/2006 | Ouchi ........................ 385/14 |
| 7,248,995 | B2 | | 7/2007 | Itsuji et al. .................. 702/150 |
| 2001/0034030 | A1 | | 10/2001 | Hefti ............................ 435/6 |
| 2002/0137032 | A1 | | 9/2002 | Hefti ............................ 435/6 |
| 2003/0040004 | A1 | * | 2/2003 | Hefti et al. .................... 435/6 |
| 2006/0039431 | A1 | | 2/2006 | Sekiguchi et al. ........ 372/44.01 |
| 2006/0085160 | A1 | | 4/2006 | Ouchi ........................ 702/150 |
| 2006/0188398 | A1 | | 8/2006 | Yano et al. .............. 422/82.01 |
| 2006/0214176 | A1 | | 9/2006 | Ouchi et al. .................. 257/98 |
| 2006/0227340 | A1 | | 10/2006 | Shioda et al. ............... 356/614 |
| 2006/0244629 | A1 | | 11/2006 | Miyazaki et al. ......... 340/855.7 |
| 2007/0030115 | A1 | | 2/2007 | Itsuji et al. .................. 340/5.8 |

FOREIGN PATENT DOCUMENTS

| | | |
|---|---|---|
| JP | 5-188013 A | 7/1993 |
| JP | 10-104171 | 4/1998 |
| JP | 2002-502028 A | 1/2002 |
| JP | 2003-509692 A | 3/2003 |
| JP | 2004-500546 A | 1/2004 |
| WO | WO 99/39190 | 8/1999 |

OTHER PUBLICATIONS

Hou-Tong Chen, et al., Terahertz imaging with nanometer resolution, Appl. Phys. Lett. vol. 83, No. 15, 2003, p. 3009-3011.

U. Schade, et al., THz near-field imaging employing synchrotron radiation, Appl. Phys. Lett. vol. 84, No. 8, 2004.02.23, p. 1422-1424.

O. Mitrofanov, et al., Study of single-cycle pulse propagation inside a terahertz near-field probe, Appl. Phys. Lett. vol. 78, No. 2, p. 252-254.

Tatsuo Nozokido, et al., Scanning Near-Field Millimeter-Wave Microscope, Laser Kenkyu, vol. 26, No. 7, 1998, p. 546-550.

Torsten Pfeifer, et al., Electro-Optic Near-Field Mapping of Planar Resonators, IEEE Transaction on Antennas and Propagation, vol. 46, No. 2, 1998, p. 284-291.

S. Hunsche, et al., Near-field time-resolved imaging with far-infrared dipole sources, Conference on Lasers and Electro-Optics '98 Technical Digest, 1998, p. 64-65.

Masahiko Tani, et al., Application of THz radiation to imaging—Research and development in Japan, US and Europe, 2002 Nen Densi Jyoho Tsushin Gakkai Sogo Taikai Koen Ronbunsyu Electronics 1, 2002, p. 491-492.

K. Tanaka, "Time-Domain Attenuated Total Reflection Spectroscopy in Tera-Herz Region", Extended Abstracts of the 51$^{st}$ Meeting of the Japan Society of Applied Physics and Related Societies, Mar. 2004, p. 31, 28p-YF-7. (with Translation).

* cited by examiner

TERAHERTZ SENSING APPARATUS USING A TRANSMISSION LINE

TECHNICAL FIELD

The present invention relates to a sensing apparatus and method for detecting physical property values or the like of an object using a high frequency electromagnetic wave in a millimeter-wave to terahertz-wave region.

BACKGROUND ART

In recent years, nondestructive sensing techniques using an electromagnetic wave o f millimeter-wave to terahertz (THz) frequencies (30 GHz to 30 THz) have been under development. Examples of techniques now under development in "application fields of the electromagnetic wave of such a frequency band include imaging a technique using a safe fluoroscopic apparatus alternative to an X-ray fluoroscope, a spectral technique for obtaining an absorption spectrum or complex dielectric constant of a material to inspect (or examine) the bonding state therein, a technique of analyzing biomolecules, and a technique for estimating a carrier concentration or mobility.

As a sensing system using a terahertz electromagnetic wave, Japanese Patent application Laid-open No. H10-104171 discloses a method of preparing a photoconductive element in which antennas also serving as electrodes are provided on a photoconductive film formed on a substrate and irradiating the photoconductive element with an extremely-short pulse laser light to generate and detect a terahertz electromagnetic wave. Since absorption lines of various materials are present in the terahertz range, it is becoming more important to apply a terahertz electromagnetic wave to sensing techniques such as analyses of plastics, composite materials, or the like, water content analysis, and biomolecule analysis. By moving an inspected (or examined) material two-dimensionally, it is also possible to obtain a two-dimensional image through imaging based on, for example, a difference in absorption coefficient of an electromagnetic wave.

In such a case, there have hitherto been such problems that optical axis alignment is required because a spatial imaging system is used, and that it is hard to increase the sensitivity when measuring a powder material or liquid material. Therefore, in recent years, there has been proposed a method of locating an inspected material on a THz-wave reflection prism and performing sensing utilizing a THz evanescent wave generated by total reflection on an upper surface of the prism (see Extended Abstracts of The 51st Meeting of The Japan Society of Applied Physics and Related Societies, 28p-YF-7). In this case, since an absorption spectrum or the like is measured based on the interaction between the evanescent wave and the inspected material, the measurement is available regardless of any form the object takes, such as liquid, power, or the like.

However, the method using the prism has limitations in reducing the beam diameter of a propagating terahertz-electromagnetic wave, so that there can typically be obtained only a maximum spatial resolution of about 100 μm which corresponds to the order of a wavelength of the terahertz electromagnetic wave. Therefore, when a two-dimensional image of an inspected object is to be observed or inspected objects are to be arranged in a two-dimensional array form, higher resolution measurement is required. Further, the use of the prism requires expensive optical parts having low-losses in the THz band, and imposes limitations in size reduction of the entire optical system. Moreover, since the optical system is liable to be affected by moisture in air, it is necessary to locate the entire optical system in a nitrogen atmosphere, thus hindering the cost reduction.

DISCLOSURE OF THE INVENTION

In view of the above problem, according to one aspect of the present invention, there is provided a sensing apparatus comprising a transmission line for propagating an electromagnetic wave therethrough; and a detection means for detecting propagation state of the electromagnetic wave at an arbitrary location on the transmission line, wherein an interaction between an object disposed in the vicinity of the transmission line and the electromagnetic wave is detected.

According to another aspect of the invention, there is provided a sensing apparatus comprising a transmission line for propagating an electromagnetic wave therethrough; a detection means for detecting propagation state of the electromagnetic wave through the transmission line; and a flow path disposed in the vicinity of the transmission line, for allowing an object to move therein, wherein an interaction between the object and the electromagnetic wave is detected.

In the present invention, for example, a THz electromagnetic wave is propagated through a distributed constant line made of a dielectric, and physical property sensing of an inspected object is performed using an electromagnetic field (such as an evanescent wave) leaked out to air in the vicinity of the transmission line. In order to obtain a high-resolution two-dimensional image, by disposing a probe for THz detection in the vicinity of the inspected object placed on the transmission line and performing scanning using the probe, it becomes possible to effect inspection with a high spatial resolution. In such a case, observation with ¹⁄₁₀ or less of the wavelength can also be effected by allowing the sensing apparatus to operate as a THz scanning nearfield optical microscope. A THz electromagnetic wave from the probe can be detected in terms of, for example, polarization variation of read light based on the Pockels effect of an electrooptic (EO) crystal.

The THz electromagnetic wave to propagate through the transmission line may be irradiated from outside of the transmission line. Alternatively, —a THz generator (electromagnetic wave generating means) may be integrated on the transmission line. In such a case, there are obtained the advantages that the electromagnetic wave is not affected by moisture in air, optical adjustment is unnecessary, and size reduction becomes possible. As the THz generator, there may be adopted a structure in which a photoconductive element is located at a portion of the transmission line, and a short-pulse laser is irradiated thereto from outside or two CW lasers having slightly different resonance frequencies are multiplexed and irradiated thereto from outside. In order to efficiently confine the THz electromagnetic wave within the THz transmission line, a distributed bragg reflector (DBR) structure or the like may further be provided on the THz transmission line. Moreover, as the light source, a structure may be used in which a small-size current injection device such as a quantum cascade laser is integrated in the vicinity of the transmission line or on the same substrate.

When a plurality of THz transmission lines are arranged in a two-dimensional array form and an inspected object is applied by inkjet or the like, it is possible to provide a chip for high-speed inspection. Further, when a multiprobe configuration is adopted, THz responses of a plurality of inspected objects can be obtained for sensing at high speed.

Other than the technique of applying an inspected object to the surface of the transmission line, it is also possible to adopt a technique such that a flow path through which a liquid can pass is formed in the vicinity of the transmission line and high-speed sensing is performed while flowing therethrough or continuously replacing an inspected liquid material.

According to the sensing apparatus and method of the present invention, even in the case of a slight amount of an inspected object, for example, spectral analysis in a region of a millimeter wave to a terahertz wave can be performed at high speed while ensuring a high degree of freedom for a sample form. In such analysis, sensing can be performed for a two-dimensional-shaped inspected object at a high spatial resolution of 100 μm or less. Further, because the small-size sensing chip is used, it is possible to provide the sensing apparatus including the entire optical system, which is small in size and low in cost.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the present invention and, together with the description, serve to explain the principles of the present invention.

BEST MODES FOR CARRYING OUT THE INVENTION

Hereinafter, although a sensing apparatus using a terahertz electromagnetic wave will be described with reference to embodiments of a photoconductive element and an integrated element including the photoconductive element, the material, structure, device, size, and the like are not limited to those described below. In addition, it is to be understood that the present invention is not limited to the particular use applications of elements and particular properties of generated electromagnetic waves disclosed herein.

EXAMPLE 1

Figure 1:
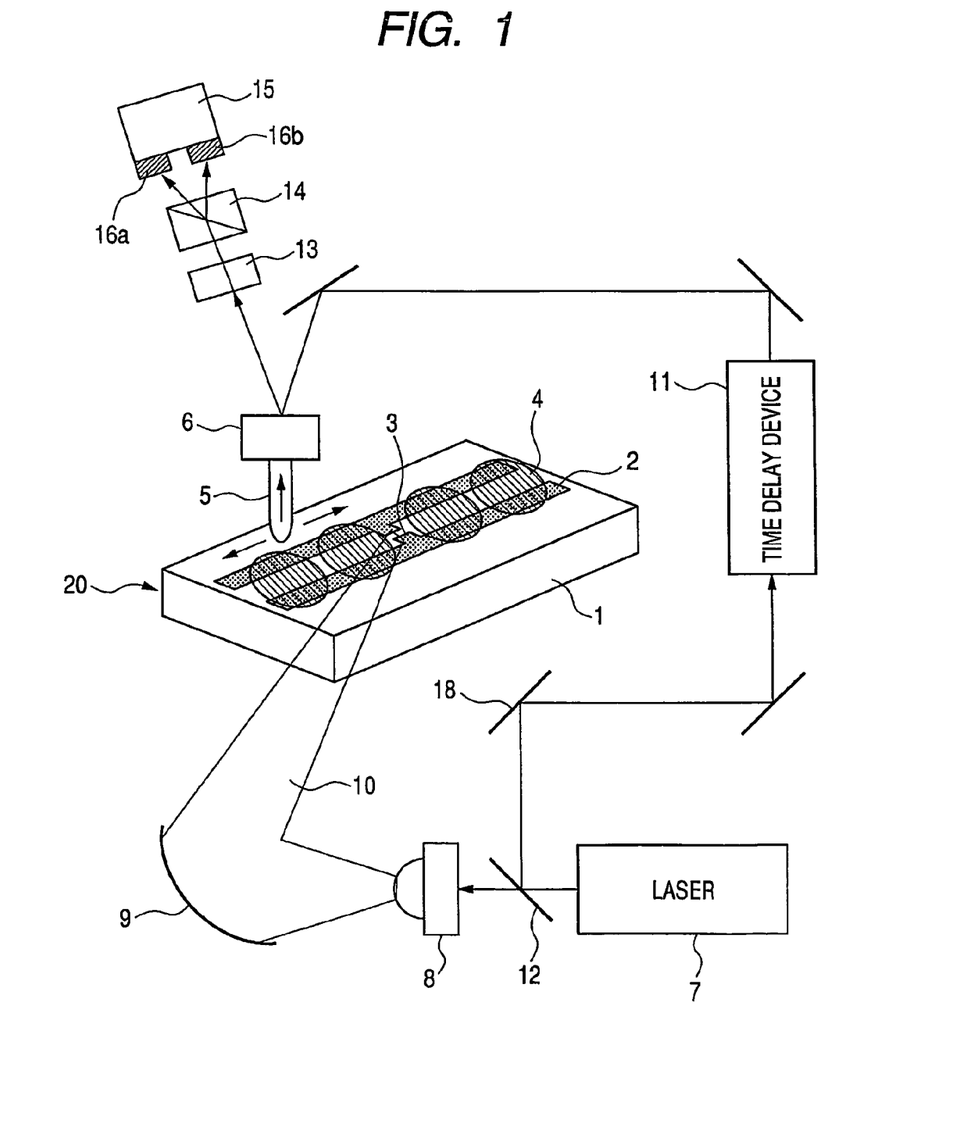
FIG. 1 is a schematic structural view showing a sensor chip and an entire system in accordance with Example 1 of the present invention.

In a first example of the present invention, a THz sensor chip and a sensing system therefor are provided as shown in FIG. 1. In a sensor chip portion 20, a transmission line 2 of a co-planar strip line structure and an antenna 3, which are made of a Ti/Au electrode, are formed on a Si substrate 1 having a thickness of 650 μm and a high resistance (>1 kΩ-cm). In this example, the electrode consists of two stripes of 20 μm in width distant by 50 μm from each other. However, the present invention is not limited to this. The antenna 3 is a dipole antenna which is used to efficiently propagate a THz electromagnetic wave 10 irradiated from outside to the transmission line 2. The THz electromagnetic wave 10 may be irradiated from the surface side on which the transmission line 2 is provided. Alternatively, the THz electromagnetic wave may be irradiated from the rear surface side of the substrate 1 because the high resistance Si has a low absorption to the THz electromagnetic wave.

Here, the substrate may be made of quartz or a resin having a low loss in the THz wavelength region. The antenna may also be a bow-tie antenna or a log-periodic antenna, which is a wideband antenna. The transmission line may be a co-planar line, a microstrip line, or the like.

The THz electromagnetic wave propagating through the transmission line 2 will interact with an inspected object 4 applied to the surface of the chip to change the propagation state or show specific dispersion characteristics, whereby physical properties can be inspected. This is because the electromagnetic wave propagates through the transmission line 2 while leaking out into air. The inspected object 4 typically has an outer size of slightly less than 100 μm and can be formed as a plurality of dots on the transmission line 2, as shown in FIG. 1 (four dots in FIG. 1, but the number of dots is not limited thereto).

In order to detect the propagation state, for example, a metal probe 5 that stands like an antenna is used. The system is configured such that components scattered by disrupting the THz electromagnetic wave propagating through the transmission line 2 are received by an electrooptic (EO) crystal 6 such as of ZnTe through the metal probe 5 For the EO crystal 6, a well-known technique for reading a change in polarization state of light, which is caused by the Pockels effect depending on the magnitude of amplitude of the THz electromagnetic wave, is used.

To explain the entire sensing system, an output of a femtosecond laser 7 having a pulse width of about 100 fsec is split into two optical paths by a splitter 12. On the excitation side, the laser is irradiated to a photoconductive antenna made of low-temperature-grown GaAs (LT-GaAs) or the like to output a THz electromagnetic wave pulse 10, which is then focused to the antenna 3 via a paraboloidal mirror 9. On the probe side, the laser is caused to enter the above-mentioned EO crystal 6 through a reflector 18 and a time delay device 11, and a reflection light modulated by the Pockels effect is caused to enter a balance receiver 15 having two light receiving portions 16a and 1βb through a quarter wavelength plate 13 and a Wollaston prism 14. The time delay device 11 is used to perform control such that the THz electromagnetic wave read by the metal probe 5 and the laser light irradiated to the EO crystal 6 are synchronized with each other to allow readout of a signal from a desired position of the inspected object. By moving the metal probe 5 to an area where an inspected object to observe is located and obtaining a signal therefrom, it is possible to obtain information related to a plurality of inspected objects on a single sensor chip 20 at high speed. In general, there is also a method of simultaneously performing plural sensings using two-dimensional image data. However, because the spatial resolution of the THz electromagnetic wave is about 100 πα which is the wavelength order, observation on a pitch equal to or less than the spatial resolution is impossible. In addition to this, improving the sensitivity has limitations, so that the concentration or volume of an inspected object cannot be made smaller than necessary values. When bio-related molecules are to be inspected, inspection using a very small amount of sample is desired. According to the method using the probe of the present invention, such limitations can be reduced. Further, when a near-field probe having a probe tip of 10 μm or less is used, a two-dimensional distribution with a spatial resolution of 10 μm or less can be obtained for a single inspected object, so that near-field precision measurement for inspecting a bonding state distribution of a polymer such as protein or DNA becomes possible.

In this example, the description has been made by taking a metallic needle probe as an example. However, the probe may be a sharpened tip of a THz transmission fiber made of a resin, a metal waveguide having a fine opening, a photonic crystal fiber, or the like. Further, when a high spatial resolution is not required, it is needless to say that a method is available in which an electrooptic crystal is directly brought close to an object.

Other than the method using an electrooptic crystal, there may be used a method using a photoconductive element, a bolometer, or other devices capable of detecting a THz electromagnetic wave.

Figure 2:
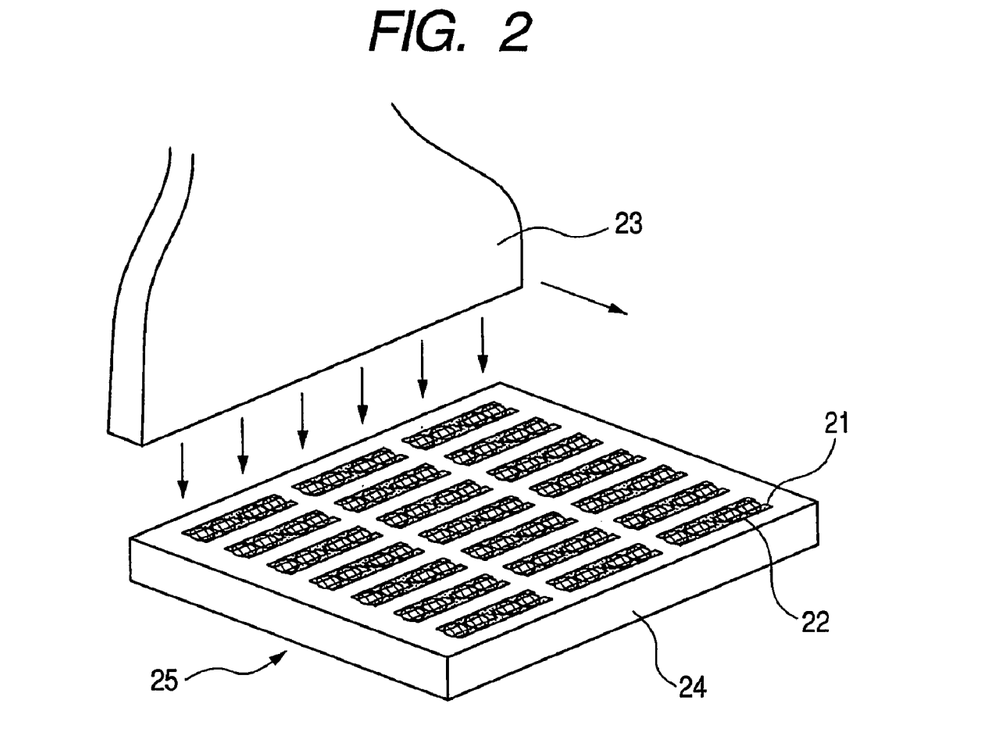
FIG. 2 is a schematic perspective view showing a two-dimensional array chip in accordance with the present invention.

FIG. 2 shows an example of a chip 25 for performing high-speed inspection having a plurality of transmission lines arranged in an array form. Transmission lines 21, each of which has the same structure as shown in FIG. 1, are arranged in a two-dimensional array form. Inspected objects 22 can be applied through an array-forming nozzle 23 at high speed by an inkjet method. A beam of a THz electromagnetic wave is spread and irradiated entirely to the rear surface of a substrate 24 (for example, 3 cm square) and coupled through an antenna provided in each of the transmission lines 21. Probes for inspection (not shown) may also be arranged in a two-dimensional array form as needed.

By adopting the probe system in this way, it is possible to flexibly deal with changes in size or system and also to provide a sensor chip having a higher spatial resolution and higher sensitivity. Further, complex processing on the chip side is unnecessary, and a disposable type sensor system, which does not need cleaning or the like, can be constructed.

EXAMPLE 2

Figure 3:
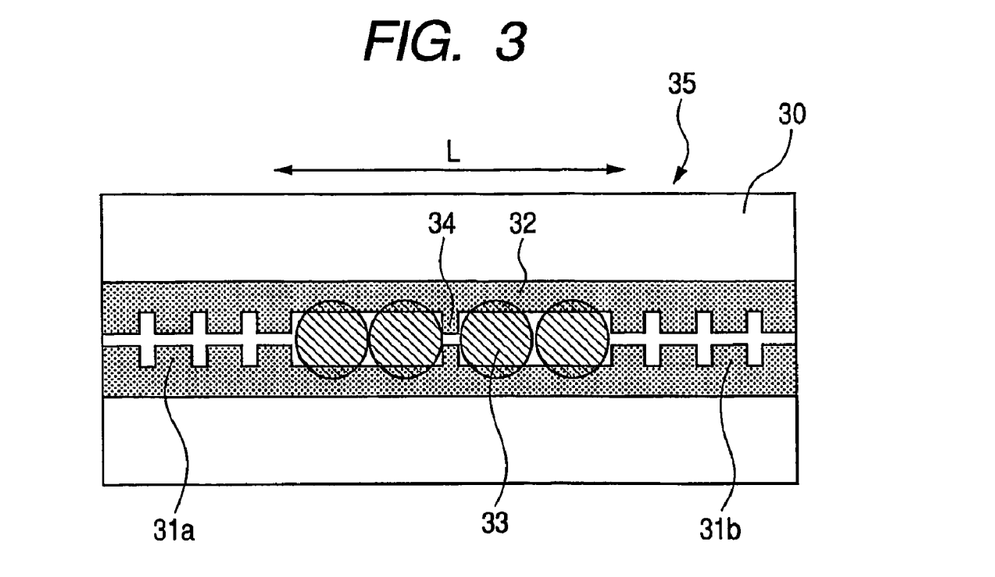
FIG. 3 is a schematic plan view showing a sensor chip having a resonant structure in accordance with Example 2 of the present invention.

In a second example of the present invention, distributed reflective regions 31a and 31b having periodic structures are provided in a transmission line 32 on a substrate 30 of a sensor chip 35 as shown in FIG. 3. By adopting such a structure, a specific frequency component of a THz electromagnetic wave irradiated from outside to an antenna 34 is efficiently confined, which is advantageous in the case where high-sensitive measurement is to be performed at a specific frequency.

Figure 4A:
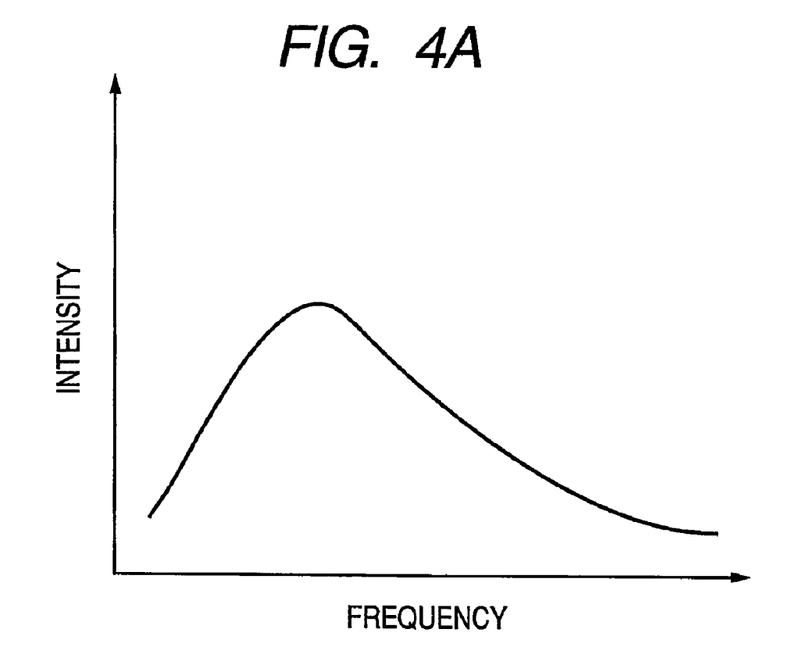
FIGS. 4A and 4B are graphical representations each for explaining a Fourier spectrum of a THz electromagnetic wave.
Figure 4B:
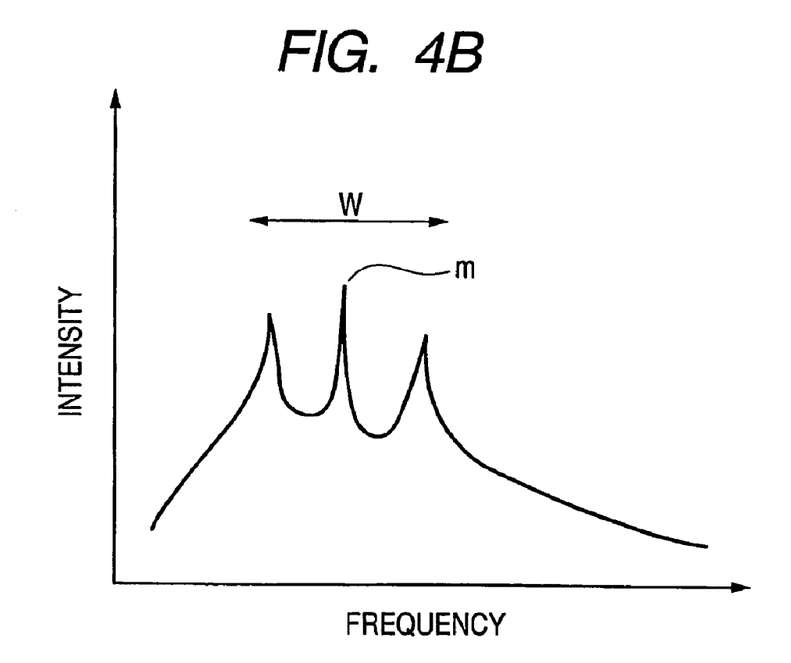

FIGS. 4A and 4B are graphical representations showing Fourier spectrum images of an electromagnetic wave in the transmission line 32 in the case where such a structure is adopted. FIG. 4A is for a THz electromagnetic pulse emitted from a photoconductive element such as shown by 8 in FIG. 1. FIG. 4B is for an electromagnetic wave confined in the transmission line in this example. A stop band produced by a DBR reflector corresponds to W, and one or more resonance modes m can be generated within the stop band depending on the length L of the sensing portion.

Because the resonance frequency is changed depending on the inspected object 33, there may be employed a method of detecting a change in the resonance point. In such a case, when a plurality of inspected objects 33 are disposed as shown in FIG. 3 there may be adopted a method of sweeping a probe such as described in Example 1 to measure both amplitude distribution and Fourier spectrum of the electromagnetic wave in the transmission line 32 and calculating the physical properties of the inspected objects 33 based on the measurements.

Further, in the case where the transmission lines are arranged in an array form as shown in FIG. 2, when the resonance frequency is set to differ depending on locations, the frequency dependence can be measured on the same chip at high speed. As the structure for confining the electromagnetic wave, a photonic crystal structure or a photonic fractal structure may be used.

EXAMPLE 3

Figure 5:
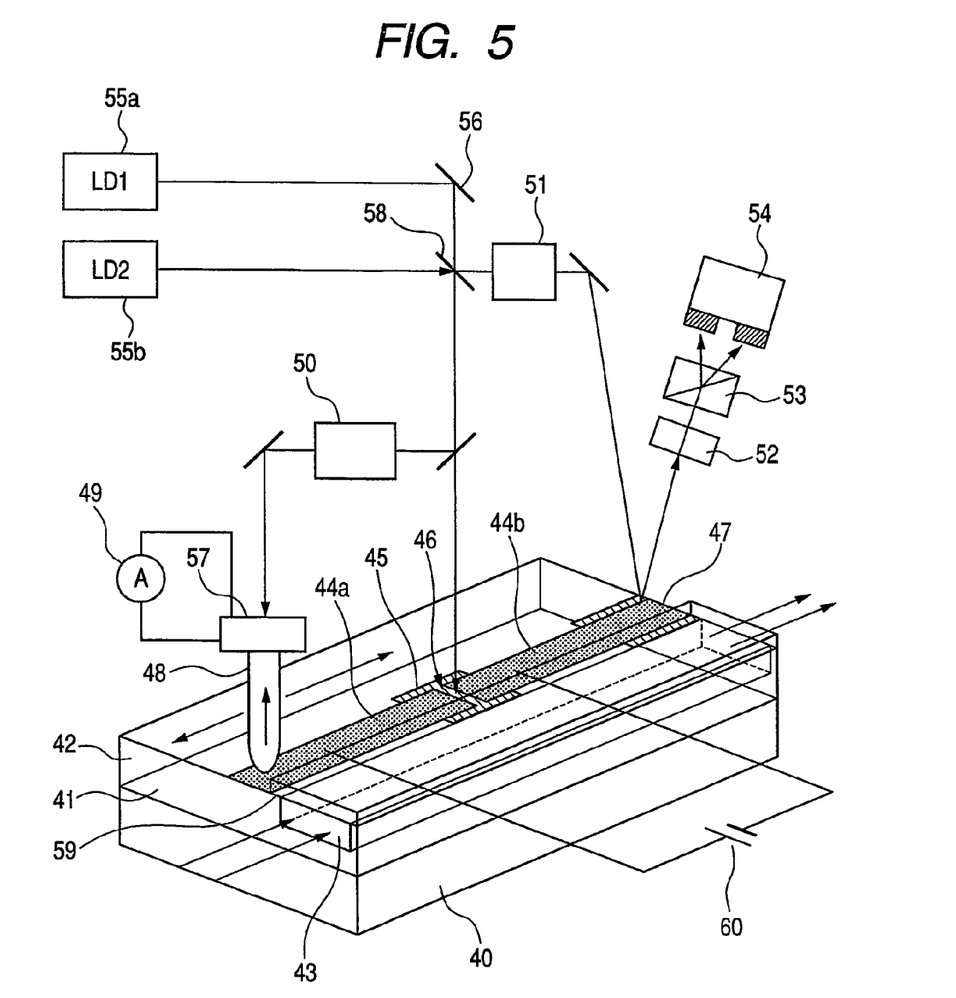
FIG. 5 is a schematic perspective view showing a sensor chip in accordance with Example 3 of the present invention.

In a third example of the present invention, unlike the method in which an inspected object is applied to the surface of a sensor chip, an inspected liquid object is caused to flow through a flow path integrally formed with a transmission line as shown in FIG. 5.

Figure 6:
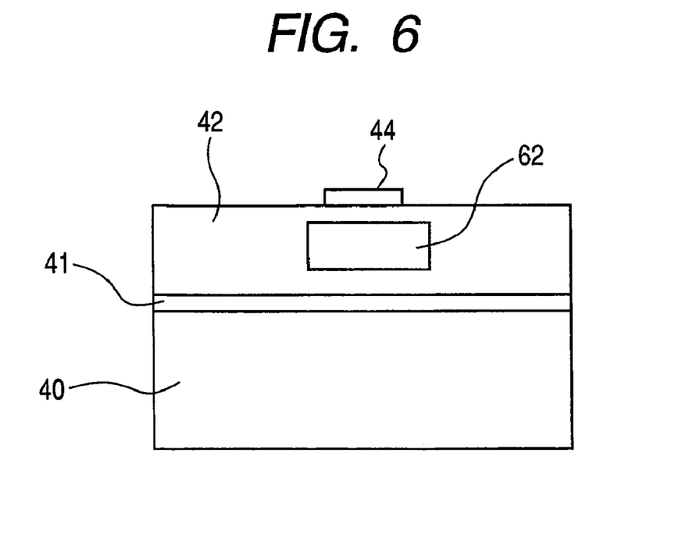
FIG. 6 is a schematic sectional view showing a modified example of the sensor chip in accordance with Example 3 of the present invention.

In the example shown in FIG. 5, signal lines 44a, 44b and an insulator 42 are provided on a Si substrate 40 with reference numeral 41 being a ground plane 41 such that a microstrip line is formed as a THz transmission line. Of course, this may be a co-planar strip line such as described in Example 1. The signal lines 44a, 44b are separated from each other by a gap portion 46, under which only an LT-GaAs epitaxial layer is transferred to form a photoconductive element 45 which generates a THz electromagnetic wave pulse by light pulse irradiation. An EO crystal 47 for detecting the transmission state may also be integrated at an end of the transmission line. A flow path 43 having a typical sectional size of 10 μm×20 μm is formed between the signal lines 44a, 44b and the ground plane 41 so as to allow a liquid as an inspected object to flow therethrough as indicated by the arrows. The liquid can be delivered by means of a micropump, an inkjet system, or the like. The structure of the flow path 43 can be produced by a method of forming a groove structure by use of a resin such as benzocyclobutene (BCB or Cyclotene (trade name)), polyimide, or polysilane, providing the groove structure with a cover 59 made of quartz glass or the like and effecting bonding. When a liquid is set but is not treated as a fluid, a simple structure without cover may be used. Further, in the example shown in FIG. 5, the groove is provided in the vicinity in the lateral direction of the signal lines as shown in FIG. 5. However, as shown in FIG. 6, a flow path 62 may be located just under a signal line 44 to improve the sensitivity.

A sensing system using the THz electromagnetic wave will be described. Although the THz pulse system using a femtosecond laser such as described in Example 1 may be used, description is made here by taking as an example a system using a THz continuous wave based on beat caused by two semiconductor lasers 55a, 55b. The two semiconductor lasers 55a, 55b are such that a difference frequency can be stabilized within the range of 0.1 to 3 THz. Two laser beams are mixed with each other by a coupler 58 through a reflector 56 and then irradiated to the gap portion 46 of the photoconductive element at a power of about 5 mW. At this time, when an electric field 60 of about 10 V is applied to the signal lines 44a, 44b, an electromagnetic wave corresponding to a beat frequency propagates through the microstrip line including the signal lines 44a and 44b. The propagating electromagnetic wave interacts with the inspected object in the flow path 43, and the state of the electromagnetic wave is detected by a detecting phot αconductive element 57 having a metal probe 48. The detection is carried out by taking out a part of the laser light from the light source, then effecting time adjustment by a time delay device 50, and measuring a current 49 by simultaneous detection. On the other hand, in the integrated EO crystal 47, the detection is performed by the same method as described in Example 1 using a time delay device 51, a quarter wavelength plate 52, a Wollaston prism 53, and a balance receiver 54.

When the beat frequency is varied, a spectrum can be observed within the range of 0.1 to 3 THz. The resonance structure such as described in Example 2 may be provided to strongly confine the electromagnetic wave.

In order to measure the characteristics of the entire fluid, the detection may be performed using the EO crystal 47. Further, in order to know the distribution in the fluid, the measurement may be performed while being scanned with the probe 48.

In this example, the measurement in a solution is possible, and THz electromagnetic wave sensing can be performed in real time in accordance with the progress of a reaction of a material.

EXAMPLE 4

Figure 7:
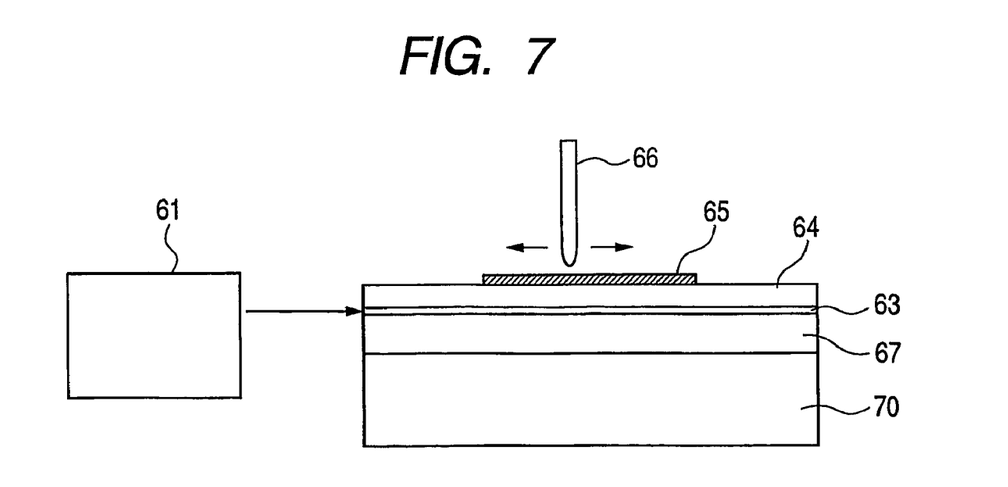
FIG. 7 is a schematic sectional view showing a sensor chip in accordance with Example 4 of the present invention.

In a fourth example of the present invention, a quantum cascade laser for a continuous wave is used as a THz light source. In FIG. 7, an electromagnetic wave from a THz laser 61 is coupled for propagation to a transmission line composed of a signal line 63 and dielectrics 64 and 67 provided on a substrate 70. The THz laser and the transmission line may be integrally formed to provide an integrated device.

An inspected object 65 is placed on the transmission line and the inspection is performed using a probe 66 in the same manner as described in the foregoing examples. Also in this case, THz near-field imaging having a spatial resolution of 10 µm or less may be performed using a near-field probe.

EXAMPLE 5

Figure 8:
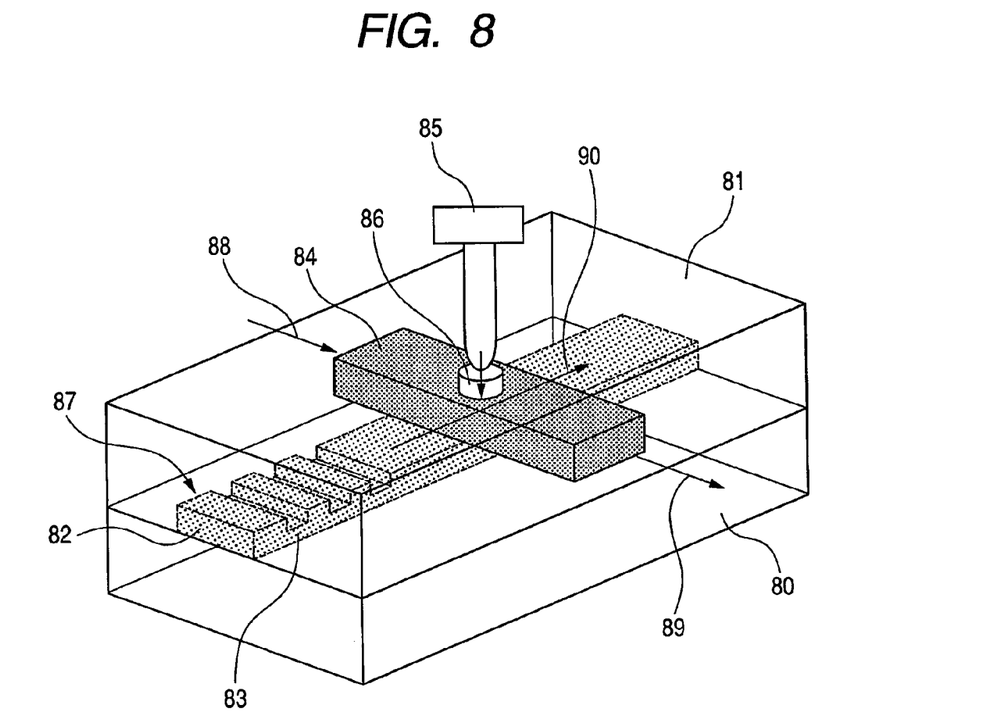
FIG. 8 is a schematic perspective view showing a sensor chip in accordance with Example 5 of the present invention.

In a fifth example of the present invention, as shown in FIG. 8, a transmission line comprises a single conductor and a flow path for moving an inspected object therethrough is disposed in the vicinity of the transmission line as with Example 3. As a dielectric substrate 80, there is used, for example, a polyolefin sheet having a thickness of 300 µm, on a surface of which an Au line 82 having a width of 10 µm and a thickness of 5 µm and an upper dielectric layer 81 made of a polyolefin sheet having a thickness of about 100 µm are formed. The Au line 82 is the so-called single line, which has a single conductor, and has good high-frequency propagation characteristics in a direction indicated by an arrow 90, which are further improved by being surrounded with the dielectric. The upper polyolefin sheet 81 is subjected to heat treatment after the formation of the Au line 82 to be bonded to the lower polyolefin sheet 80. Alternatively, the upper dielectric layer 81 may be formed by application of a liquid organic material onto the substrate 80 in a large film thickness followed by curing.

Further, there is formed in the dielectric layer 81 a flow path 84 for putting the inspected object therein, and the inspected object is charged in the direction shown by the arrow 88 and discharged in the direction shown by the arrow 89. Incidentally, the space for containing the inspected object does not necessarily need to be in a flow path form and a vessel only for housing the inspected object may be provided instead. The shape and size of the flow path is, for example, a square with a side length of about several 10 µm, and in order to allow a detecting probe 85 to be inserted into the flow path 84, a hole 86 with a diameter of about 10 µm is formed in the vicinity of an intersection of an inspected object portion (flow path 84) and the transmission line (Au line 82). A probe 85 such as described in the foregoing examples may be inserted into the hole 86 to detect the propagation state of an electromagnetic wave. Here, when the hole has such a large size as to allow the probe to scan therein, a distribution state of the inspected object can also be examined.

The method of coupling an electromagnetic wave to this sensing chip and performing the detection may be the same as described in the foregoing examples. However, the coupling of a terahertz electromagnetic wave 87 to the single line may also be effected by means of a diffraction grating 83 formed on the line 82. Further, the coupling means is not limited to the diffraction grating and also includes an antenna or the like. Moreover, there may also be adopted a method of integrating a photoconductive element into this sensing chip and irradiating the element with light from outside.

In order to confine an electromagnetic wave in the vicinity of the inspected object portion, a photonic crystal structure or a photonic fractal structure (both not shown) may be formed using a dielectric in the vicinity of the intersection of the flow path 84 and the transmission line 82, or a diffraction grating may also be formed on the other end of the transmission line 82 to provide a resonance structure, whereby the sensitivity can be improved.

As many apparently widely different embodiments of the present invention can be made without departing from the spirit and scope thereof, it is to be understood that the present invention is not limited to the specific embodiments thereof except as defined in the claims.

This application claims priority from Japanese Patent Application Nos. 2004-223665 filed Jul. 30, 2004 and 2005-154772 filed May 27, 2005, which are hereby incorporated by reference herein.

The invention claimed is:

1. A sensing apparatus comprising:
   a transmission line for propagating an electromagnetic wave therethrough; and
   a detection unit for detecting a propagation state of the electromagnetic wave at an arbitrary location on the transmission line,
   wherein an interaction between an object disposed in the vicinity of the transmission line and the electromagnetic wave is detected, and
   wherein the transmission line has a resonance structure for confining the propagating electromagnetic wave, and the resonance structure comprises a distributed reflective region having a periodic structure.

2. The sensing apparatus according to claim 1, further comprising an electromagnetic wave generating unit.

3. The sensing apparatus according to claim 2, wherein the transmission line and the electromagnetic wave generating unit are disposed on a same substrate.

4. The sensing apparatus according to claim 2, wherein the electromagnetic wave generating unit is of a current-injection type.

5. The sensing apparatus according to claim 1, wherein the detection unit comprises a thin-line-shaped probe.

6. The sensing apparatus according to claim 1, wherein the detection unit comprises a probe with a tip of a diameter which is not more than 1/10 of a wavelength of a propagating electromagnetic wave.

7. The sensing apparatus according to claim 1, wherein the detection unit detects the propagation state on the transmission line at a plurality of locations.

8. The sensing apparatus according to claim 7, wherein the detection unit detects the propagation state of the electromagnetic wave at the plurality of locations by changing a relative positional relationship between the detection unit and the transmission line by scanning.

9. The sensing apparatus according to claim 7, wherein the detection unit that detects the propagation state of the electromagnetic wave at the plurality of locations comprises an electrooptic crystal.

10. A sensing apparatus according to claim 1, wherein the electromagnetic wave has a frequency within the range of 30 GHz to 30 THz.

11. A sensing apparatus comprising:
a transmission line for propagating an electromagnetic wave therethrough;
a detection unit for detecting a propagation state of the electromagnetic wave through the transmission line; and
a flow path disposed in the vicinity of the transmission line, for allowing an object to move therein,
wherein an interaction between the object and the electromagnetic wave is detected, and
wherein the transmission line has a resonance structure for confining a propagating electromagnetic wave, and the resonance structure comprises a reflective region having a periodic structure.

12. The sensing apparatus according to claim 11, wherein the detection unit is provided at a plurality of locations.

13. The sensing apparatus according to claim 11, wherein the electromagnetic wave has a frequency within the range of 30 GHz to 30 THz.

* * * * *